US011432997B2

(12) United States Patent
Zhang et al.

(10) Patent No.: US 11,432,997 B2
(45) Date of Patent: Sep. 6, 2022

(54) STERILE DRUG DISPENSING SYSTEM AND STERILE DRUG DISPENSING METHOD

(71) Applicant: Harbin Biyan Technology Co., Ltd., Harbin (CN)

(72) Inventors: Jin Dong Zhang, Harbin (CN); Wei Zhang, Harbin (CN)

(73) Assignee: Harbin Biyan Technology Co., Ltd., Harbin (CN)

(*) Notice: Subject to any disclaimer, the term of this patent is extended or adjusted under 35 U.S.C. 154(b) by 282 days.

(21) Appl. No.: 16/478,478

(22) PCT Filed: Jun. 27, 2017

(86) PCT No.: PCT/CN2017/090297
§ 371 (c)(1),
(2) Date: Jul. 17, 2019

(87) PCT Pub. No.: WO2018/133327
PCT Pub. Date: Jul. 26, 2018

(65) Prior Publication Data
US 2020/0188229 A1 Jun. 18, 2020

(30) Foreign Application Priority Data
Jan. 17, 2017 (CN) .......................... 201710032058.8

(51) Int. Cl.
*A61J 1/20* (2006.01)
*A61M 5/20* (2006.01)

(52) U.S. Cl.
CPC ............. *A61J 1/2082* (2015.05); *A61J 1/201* (2015.05); *A61M 5/20* (2013.01); *A61M 5/2053* (2013.01)

(58) Field of Classification Search
CPC ........ A61J 1/2082; A61J 1/201; A61J 1/2096; A61J 1/2089; A61M 5/20; A61M 5/2053
See application file for complete search history.

(56) References Cited

U.S. PATENT DOCUMENTS

| 5,017,186 | A | * | 5/1991 | Arnold | A61J 1/2096 141/48 |
| 10,781,001 | B2 | * | 9/2020 | Min | B65B 3/003 |
| 2020/0046899 | A1 | * | 2/2020 | Cane' | B65B 3/003 |

FOREIGN PATENT DOCUMENTS

| CN | 105796340 A | * | 7/2016 |
| CN | 205626501 U | * | 10/2016 |

OTHER PUBLICATIONS

Machine translation of CN105796340A (Year: 2022).*
Machine translation of CN205626501U (Year: 2022).*

* cited by examiner

Primary Examiner — Timothy P. Kelly

(57) ABSTRACT

A sterile drug dispensing system, comprising: an air source output device, a handle and a drug dissolving device; the drug dissolving device is detachably mounted on the handle, the handle being connected to the air source output device by means of a power line and an air pipe, being for use in filtering gas and controlling the gas source output device; the gas source output device is used for outputting and extracting gas. A sterile drug dispensing method, which corresponds to the operating steps of the sterile drug dispensing system.

8 Claims, 9 Drawing Sheets

STERILE DRUG DISPENSING SYSTEM AND STERILE DRUG DISPENSING METHOD

BACKGROUND OF THE INVENTION

Field of the Disclosure

The present invention relates to the field of dug dispensing equipment, in particular to a sterile drug dispensing system and a sterile drug dispensing method thereof.

Description of Related Art

Nowadays, drug dispensing in hospitals relies mainly on manual operations, most of which are carried out in an open space. Such operations can easily cause various air and bacteria in the air to enter the drug, causing drug contamination. The most common way of drug dispensing for clinical infusion is manual dispensing, wherein a nurse has to manually use a syringe to mix the liquid medicine, powder, etc. in a vial with other liquid medicine, and then inject the mixture into an infusion bottle or a patient. During this process, the nurse has to continuously operate the drug dispensing device to perform the work of withdrawing and sucking the liquid medicine, which requires high-intensity labor, but has low efficiency. More importantly, for traditional drug dispensing devices and drug dispensing methods, bacteria are easy to be brought into the drug dispensing system due to exposure to the air, and the drug dispensing device has poor airtightness, which cannot achieve a sterile effect and is likely to cause contamination of the drug.

In view of the above-mentioned defects, the inventors of the present invention have finally obtained the present invention through a long period of research and practice.

SUMMARY OF THE INVENTION

In order to solve the above technical defects, the technical solution adopted in the present invention is to provide a sterile drug dispensing system, including an air source output device, a handle, and a drug dissolving device. The drug dissolving device is detachably mounted on the handle.

The handle is connected to the air source output device through a power cord and an air pipe, for filtering air, and controlling the air source output device. The air source output device is used to output and extract air.

A sterile drug dispensing method includes steps of: preparing the above-mentioned sterile drug dispensing system, wherein the drug dissolving device includes a needle, a barrel, and a rubber stopper. The rubber stopper is disposed inside the barrel. A filter is disposed in the handle.

The method includes the following steps.

Step S6: Inserting a needle of the drug dissolving device into a vial, controlling a rubber stopper in the drug dissolving device to move away from the needle, pumping a liquid medicine in the vial into the drug dissolving device, and pulling out the needle.

Step S7: Inserting the needle of the drug dissolving device into a new vial, if the new vial is filled with a liquid medicine, controlling a rubber stopper in the drug dissolving device to move away from the needle, and pumping the liquid medicine in the new vial into the drug dissolving device, and pulling out the needle; and if the new vial is filled with a powder medicine, controlling the rubber stopper to move toward the needle, pushing the liquid medicine into the new vial, and pulling out the needle after mixing.

Step S8: Repeating the previous step until the liquid medicine in all vials is pumped into the drug dissolving device.

It's characterized that, a certain distance is reserved between the rubber stopper and the front end of the barrel in the drug dissolving device to counter the negative pressure in the vial.

Preferably, in Step 6 and Step 7, the handle controls the air source output device to extract the air at the rear end of the rubber stopper in the barrel to form a negative pressure environment, so that the rubber stopper moves away from the needle. The handle controls the air source output device to output air to the rear end of the rubber stopper in the barrel to form a positive pressure environment, so that the rubber stopper moves toward the needle.

Preferably, before Step S6, the method further includes Step S5: mounting the drug dissolving device on the handle.

Preferably, before Step S5, the method further includes the following steps.

Step S1: An air source output device outputting a small power air source to the handle, the small power air source replacing a front end region of the handle with a clean and sterile environment after passing through the filter in the handle.

Step S2: Attaching the drug dissolving device to the inside of the front end of the handle and pushing backwards until the rear end of the drug dissolving device enters the sterile environment at the front end of the handle.

Step S3: Mounting the drug dissolving device rearward on the handle while controlling the air source output device to stop providing the small power air source to the handle.

Preferably, in Step S1, the rubber stopper of the drug dissolving device is located at the end of the drug dissolving device, and the end of the drug dissolving device is on the same plane as the rubber stopper.

Preferably, in Step S2, after the rear end of the drug dissolving device enters the sterile environment at the front end of the handle, it is left for 1-2 seconds to continue mounting.

Preferably, in Step S3, when the drug dissolving device is pushed to the groove of the front end of the handle, the drug dissolving device is snapped into the groove of the front end of the handle, and the drug dissolving device is rotated, so as to achieve a snap connection between the drug dissolving device and the handle.

Preferably, in Step 3, a detection unit is disposed on the handle, for detecting that the drug dissolving device has been mounted on the handle, and controlling the air source output device to stop providing a small power air source to the handle.

Preferably, after Step S3, the method further includes Step S4: the air source output device outputting air, and controlling the rubber stopper to move to an intermediate position of the barrel.

Preferably, the handle controls the air source output device through buttons, and the buttons are disposed on the handle.

The advantages of the present invention compared to the prior art are: the present invention provides a sterile drug dispensing system, including an air source output device, a handle and a drug dissolving device. The sterile drug dispensing system of the present invention has the advantages of simple and reasonable structure, good sealing property, easy disassembly and assembly, convenient replacement, safety and reliability, high filtering efficiency, may provide uniform, slow, non-crossing, large-area clean air, and may replace the front end of the handle with a clean and sterile environment for achieving a local level of cleanliness. Through air replacement, the sterile filtering method of the present invention ensures that the drug dissolving device before mounting and during the dispensing, is clean and sterile, safe and reliable, high-efficient in filtration, safe, clean and sterile in filtration, effective in filtration, with reduced labor intensity and wide applicability.

BRIEF DESCRIPTION OF THE DRAWINGS

In order to more clearly illustrate the technical solutions in various embodiments of the present invention, the drawings used in the description of the embodiments will be briefly described below.

DESCRIPTION OF THE INVENTION

The above and other technical features and advantages of the present invention are described in more detail below with reference to the accompanying drawings.

Embodiment 1

Figure 1:
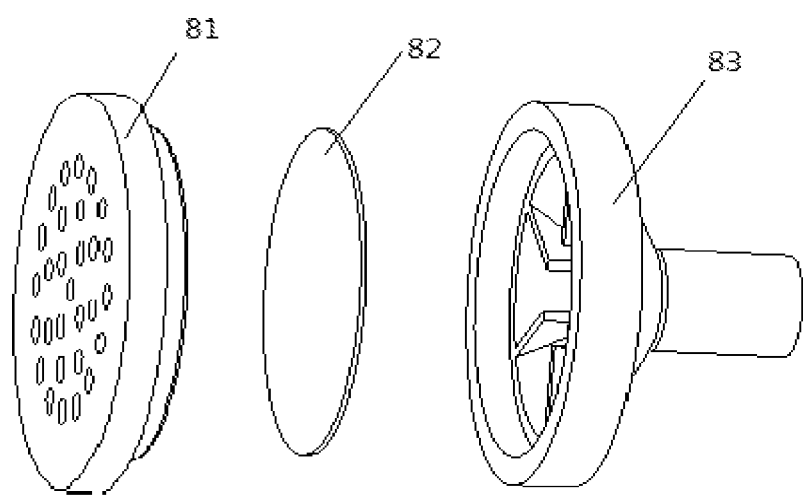
FIG. 1 is a structural view of a filter according to Embodiment 1 of the present invention.

As shown in FIG. 1, a structural view of a filter provided in the present invention is illustrated. The filter of the present invention includes an upper shell, a lower shell, and a filter film 82. The upper shell is fixedly connected to the lower shell, and the filter film 82 is disposed in a cavity between the lower shell and the upper shell. The upper shell and the lower shell are also referred to as a filter upper shell 81 and a filter lower shell 83.

The filter lower shell 83 has a tapered shape, and is provided evenly with reinforcing ribs on an inner wall thereof for improving the strength of the filter lower shell 83, and cooperates with the filter upper shell 81 to sandwich the filter film 82. The clean air enters through a small opening of the tapered filter lower shell 83.

The filter upper shell 81 is of a circular buckle cover structure matched with a large opening of the filter lower shell 83, and is fastened to the filter lower shell 83. The filter upper shell 81 is provided with a certain number of small holes with same diameters as air outlets, which may increase the air flow area; the air outlets are evenly distributed, and may provide a large area of clean air that is relatively slow, uniform, does not cross each other, and has no eddy currents and no turbulence. The filter upper shell 81 has a diameter of 2.5 cm and may produce an air beam with a diameter of 2.5 cm to replace the front end of the air outlets with a clean environment for achieving a local sterile effect. The surface of the filter upper shell 81 is flat, that is, the other surfaces on the filter upper shell 81 except the surface outside the air outlets are in the same plane with no protrusions or grooves existing, so as to avoid eddy currents and dead angles, thereby preventing contamination by contaminants and ensuring a sterile environment. One side of the filter upper shell 81 adjacent to the filter lower shell 83 is provided with reinforcing ribs for improving the strength of the filter upper shell 81, and the filter upper shell 81 cooperates with the filter lower shell 83 to sandwich the filter film 82. The provision of the reinforcing ribs on the filter improves the overall strength while sandwiching the filter film 82 in the middle to prevent the film from being broken, and to improve the filtration efficiency. The number of the reinforcing ribs of the filter upper shell 81 is two, and may also be one or more. The number of reinforcing ribs of the filter lower shell 83 is six, and of course, may also be less than or more than six. Flexible provision of different numbers of reinforcing ribs is to meet different requirements in different designs. In the present embodiment, the reinforcing ribs on the filter upper shell 81 and the filter lower shell 83 are all in an I-shape. Of course, other shapes with a curvature or an angle may be used, that is, the shape of the reinforcing ribs may be specifically configured according to actual requirements.

The filter film 82 is disposed between the filter upper shell 81 and the filter lower shell 83. The filter film 82 of the present invention adopts polytetrafluoroethylene filter film with a pore size of 0.22 mm, which is versatile and low cost, and has a pore size being the threshold of sterile filtration so as to function well in filtering the air.

When the filter is blew with an air, the lower shell 83 acts as an air inlet, the upper shell 81 acts as an air outlet, and the air enters from the small opening of the filter lower shell 83, is filtered by the filter film 82 and is blown out from each of the small holes of the filter upper shell 81 after becoming a clean air. The air beam blown from the filter upper shell 81 may be up to 2.5 cm in diameter to increase the air output area, and have a slow, uniform, non-intersecting airflow without eddy currents and turbulence, which may replace the area of the front end of the filter upper shell 81 with a clean and sterile environment for achieving a local level of cleanliness The filter structure of the present invention is simple and reasonable, wherein the filter upper shell 81 adopts a circular cover with small holes so as to reduce the resistance of the air flowing through the filter and provide a uniform, slow, non-crossing, large area of clean air for achieving a local clean and sterile effect on the front end of the filter with high filtration efficiency and good effect.

Embodiment 2

The filter of the present embodiment is different from Embodiment 1 in that the filter of the present embodiment further comprises a positioning member. The positioning member is disposed between the filter upper shell 81 and the filter lower shell 83 for sandwiching the filter film 82.

The positioning member of the present embodiment is a circular structure having the same diameter as the filter film 82, and the surface of the positioning member is provided with air outlet holes respectively corresponding to the filter upper shell 81, which is disposed in the cavity between the filter upper shell 81 and the filter lower shell 83 and disposed coaxially with the filter film 82 with a thickness adapted to the remaining amount of the cavity between the filter upper shell 81 and the filter lower shell 83 so as to sandwich the filter film 82. After the positioning member is disposed, when the filter is blew with an air, the lower shell 83 acts as an air inlet, the upper shell 81 acts as an air outlet, and the air enters from the small opening of the filter lower shell 83, through the filter film 82 via the positioning member, is filtered by the filter film 82 and is blown out from each of the small holes of the filter upper shell 81 after becoming a clean air. The air beam blown from the filter upper shell 81 may be up to 2.5 cm in diameter to increase the air output area, and have a slow, uniform, non-intersecting airflow without eddy currents and turbulence, which may replace the area of the front end of the filter upper shell 81 with a clean and sterile environment for achieving a local level of cleanliness Sandwiching and fixing the filter film 82 by adding the positioning member may prevent contamination caused by displacement or bending of the filter film 82 in the cavity formed by the filter upper shell 81 and the filter lower shell 83 due to the action of the air source and hence loss of air filtering function, and may increase the service life of the filter.

Embodiment 3

Figure 2:
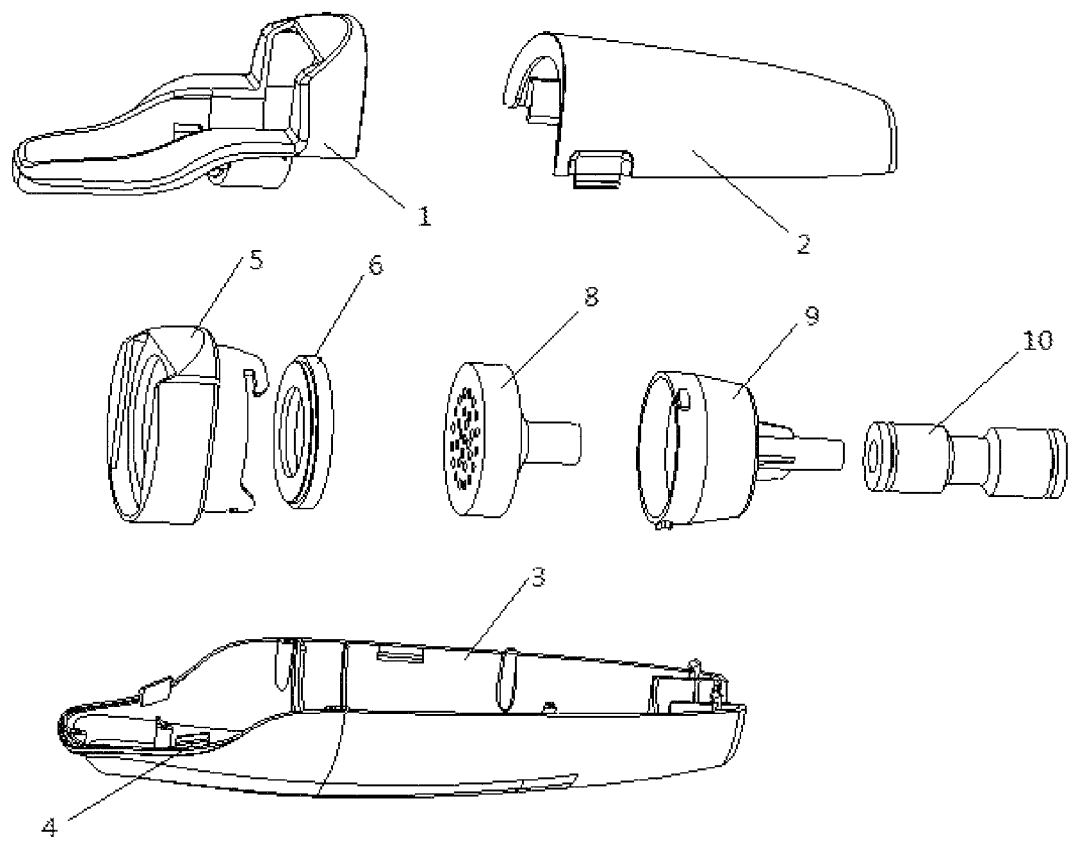
FIG. 2 is an exploded structural view of a handle according to Embodiment 3 of the present invention.

As shown in FIG. 2, an exploded structural view of a handle according to Embodiment 3 of the present invention is illustrated. The handle of the present embodiment includes the filter 8 of Embodiment 1 or Embodiment 2, and further includes a housing, a sealing fixture part, and a connecting member. The sealing fixture part is disposed inside the housing and is sealingly and fixedly connected with the filter for ensuring the airtightness of the air passage inside the handle. One end of the connecting member is connected to the filter inside the housing, and the other end is connected to the air pipe outside the housing.

The housing includes an outer case and a control unit, and the control unit is disposed on the outer case for controlling an air source output device to blow air to and pump air from the handle. The outer case includes an upper cover, a surface cover 2 and a bottom case 3, and the surface cover 2 and the bottom case 3 are connected by a buckle to facilitate disassembly. The upper cover is disposed on the inner side of the front end of the bottom case 3, and the two are cooperated as a front end component of the handle for fixing the drug dissolving device. The front end component of the handle is protruded for the user to hold, and the protruding form may be designed differently according to the optimal effect of the actual situation so as to obtain a better user experience. The outer arc of the upper cover is the same as the inner arc of the bottom case 3, and the inner arc of the upper cover is the same as the outer arc of the drug dissolving device, so that the drug dissolving device may be completely adhered to the inner side of the upper cover when the drug dissolving device is mounted, and so that the drug dissolving device and the handle are more firmly attached to avoid air leakage and ensure airtightness. The upper cover is provided with a groove thereon, and when the drug dissolving device is mounted on the handle, a side flap of the drug dissolving device is caught in the groove; at this time, the drug dissolving device is coaxial with the handle, and then the drug dissolving device is rotated by 90 degrees, so that the drug dissolving device is engaged with the handle. The control unit is a button, which is disposed on the bottom case 3, and the number of the buttons is at least two for controlling the air passage output device to blow air to and pump air from the handle.

The sealing fixture part includes a filter head 5, a movable plug 6 and a filter tail 9. The movable plug 6 is engaged with the filter upper shell 81 of the filter, the shape of the filter tail 9 is adapted to that of the filter 8, the filter is disposed in the filter tail 9, and the filter head 5 is directly buckled on the filter tail 9. When the drug dissolving device is mounted on the handle, the tail of the drug dissolving device is fixed into the movable plug 6 as the tail of the drug dissolving device reaches the filter head 5, and the drug dissolving device is rotated by 90 degrees to cause the tail of the drug dissolving device to rotate within the movable plug 6 while the movable plug 6 being not rotated with the tail of the drug dissolving device, so as to complete the fixing and mounting between the drug dissolving device and the handle.

The connecting member is a double-headed air pipe joint 10. One end of the double-headed air pipe joint 10 is connected to the filter by connecting the filter tail 9, and the other end thereof is connected to a closed air pipe. The double-headed air pipe joint 10 is a quick joint, which has the advantages of being easy to insert and remove, and having good sealing property.

In the present embodiment, the handle is connected to the air source output device through the air pipe and the power cord. Before the drug dissolving device is mounted to the handle of the present embodiment, the air source output device provides the handle with a small power air source, which enters the filter lower shell 83 through the air pipe and is filtered by the filter film 82 to obtain a clean and sterile air, and the filtered air passes through the filter upper shell 81 and is blown out from the small air outlets of the filter upper shell 81 to obtain a clean air which provides uniform, slow, non-crossing and large area, so that the area of the front end of the filter upper shell 81 may be replaced with a clean and sterile environment for achieving a local level of cleanliness. When the drug dissolving device is mounted to the handle, the front end of the handle is kept to be blown and supplied with a small power air source, the front end area of the handle is replaced with a clean and sterile environment, the drug dissolving device is attached to the inside of the front end of the handle, and then the drug dissolving device is hold and squeezed against the handle while advancing it toward the filter; when advancing to a position closer to the front end of the handle, the drug dissolving device is advanced after 1-2 seconds until the drug dissolving device is fixed with the movable plug 6 in the filter head of the sealing fixture at the groove at the front end of the handle to ensure that the small power air source blows the end of the drug dissolving device to become sterilized, and the drug dissolving device is rotated to fix the drug dissolving device on the handle; at this time, the supply of a small power air source to the handle is stopped, and the air passage output device is controlled by the button to blow air to and pump air from the handle for dispensing.

Embodiment 4

Figure 3:
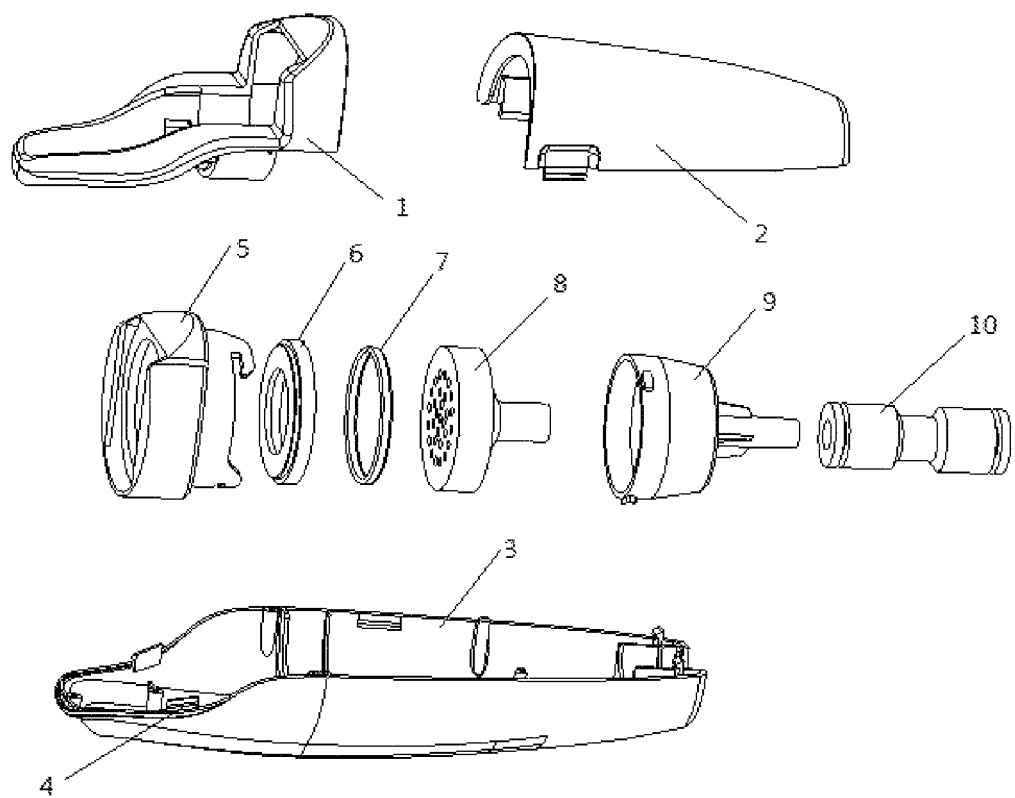
FIG. 3 is an exploded structural view of a handle according to Embodiment 4 of the present invention.

As shown in FIG. 3, an exploded structural view of a handle according to Embodiment 4 of the present invention is illustrated. A handle of the present embodiment is different from Embodiment 3 in that the sealing fixture part of the handle of the present embodiment further includes an O-ring 7. The O-ring 7 is disposed between the filter and the movable plug 6 for preventing hard grinding and for buffering.

The movable plug 6 is buckled on the filter upper shell 81 of the filter, and the O-ring 7 is disposed between the movable plug 6 and the filter; the intermediate diameter of the O-ring 7 is configured to 2 cm, which is consistent with the drug dissolving device. It is used to prevent hard grinding and for buffering, thereby increasing the service life of the movable plug 6.

Embodiment 5

Figure 4:
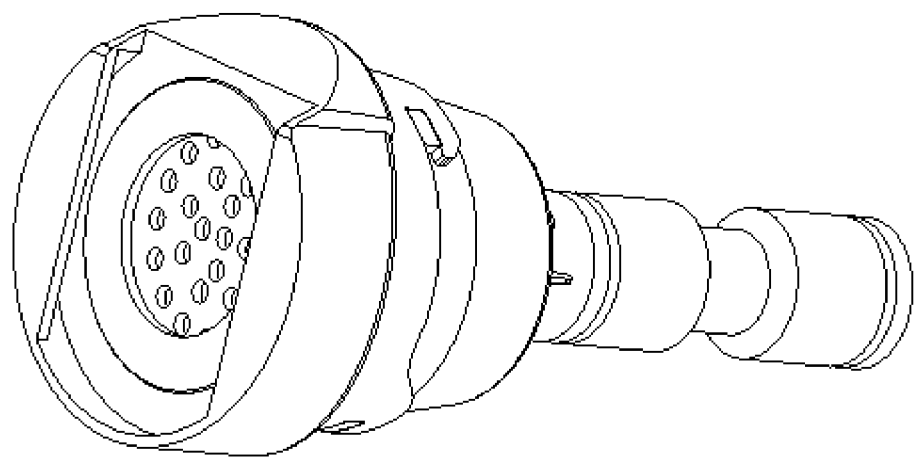
FIG. 4 is a structural view showing an assembly of a sealing fixture part and a filter according to Embodiment 5 of the present invention.

As shown in FIG. 4, a structural view showing an assembly of a sealing fixture part and a filter according to Embodiment 5 of the present invention is illustrated. A handle of the present embodiment is different from Embodiment 4 in that the filter head 5 in the sealed sealing fixture part of the present embodiment is directly snapped onto the filter tail 9, so that the filter head 5, the movable plug 6, the O-ring 7, the filter, and the filter tail 9 are assembled into an air passage assembly that may be integrally assembled and replaced.

The filter head 5 is in a snap connection with the filter tail 9, which has achieved a fast and stable fixed connection and ensures airtightness. Of course, the filter head 5 may also be in a plug connection, a screw connection or the like with the filter.

The sealing fixture part and the filter are assembled into an air passage assembly that may be assembled and replaced in an integrated manner, and various components of the air passage assembly may be manufactured separately and assembled into a replacement for integrally disassembling and assembling. The frequency of replacement is once a day, which allows quick installation and removal of the air passage assembly to ensure a sterile environment and air tightness, improved work efficiency and simplified operation steps.

Embodiment 6

A handle of the present embodiment is different from Embodiment 3 in that the movable plug 6 of the sealing fixture part of the present embodiment is buckled on the filter. When the drug dissolving device is mounted on the handle, the tail of the drug dissolving device is fixed into the movable plug 6 as the tail of the drug dissolving device reaches the filter head 5, and the drug dissolving device is rotated by 90 degrees to cause the movable plug 6 to be rotated with the tail of the drug dissolving device, so as to better seal the tail of the drug dissolving device with the sealing fixture part in the handle, further enhancing air tightness.

Embodiment 7

Figure 5:
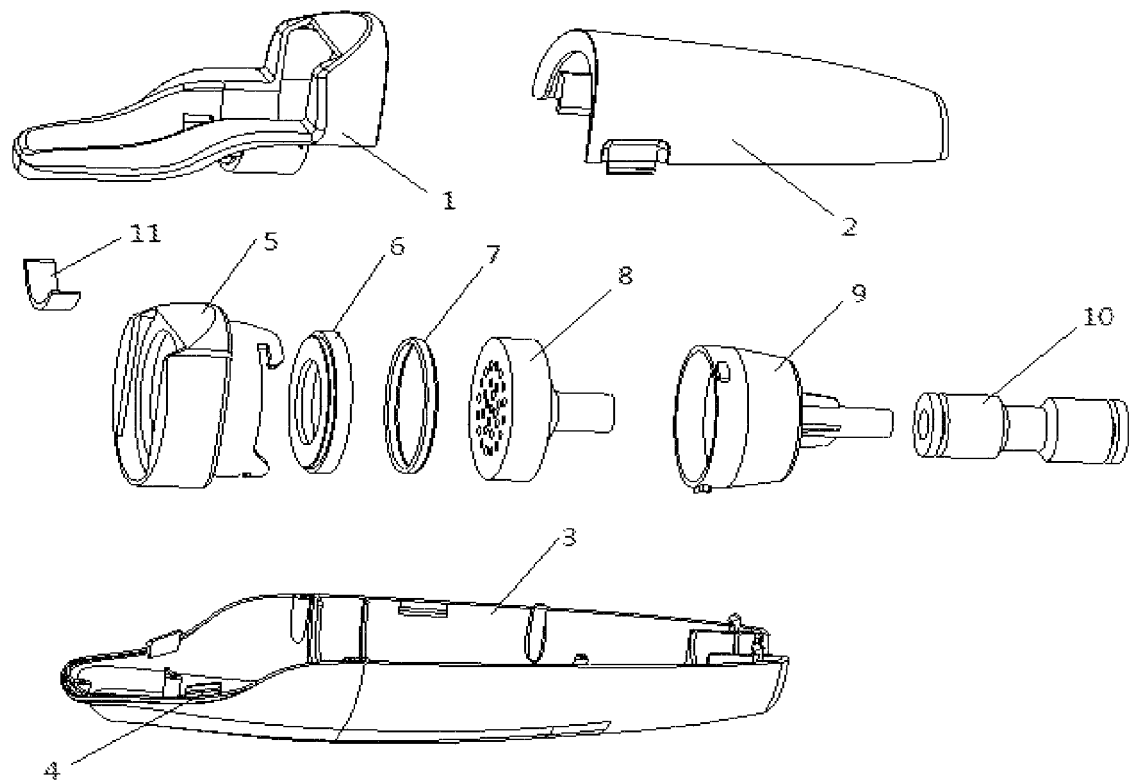
FIG. 5 is an exploded structural view of a handle according to Embodiment 7 of the present invention.

As shown in FIG. 5, an exploded structural view of a handle according to Embodiment 7 of the present invention is illustrated. A handle of the present embodiment is different from Embodiment 3 in that the handle of the present embodiment further includes a detection unit. The detection unit is disposed on the outer case for detecting information on the mounting position of the drug dissolving device and transmitting the information to the air source output device.

The detection unit includes a light-transmitting lens 11 and a photoelectric sensor. The light-transmitting lens 11 is disposed at a position on the upper cover at a certain distance from the air passage assembly for causing the photoelectric sensor located inside thereof to read the information of a strip disposed at the corresponding position of the drug dissolving device. The distance from the strip on the drug dissolving device to the rear end of the drug dissolving device is the same as the distance between the light-transmitting lens 11 and the air passage assembly. After the drug dissolving device is mounted on the handle, the strip on the dissolver covers the light-transmitting lens 11 to trigger the photoelectric sensor, and then the photoelectric sensor sends a signal to a control air passage output device for causing the control air passage output device to stop supplying the small power air source. The setting of the detection unit may accurately detect whether the drug dissolving device is mounted to the specified position, and quickly control the relevant electromagnetic valve in the air source output device to stop providing a small power air source but supplying a large power air source into the handle after determining that the drug dissolving device is mounted to the specified position, so as to simplify the operation steps, speed up the dispensing process and improve work efficiency.

Embodiment 8

Figure 6:
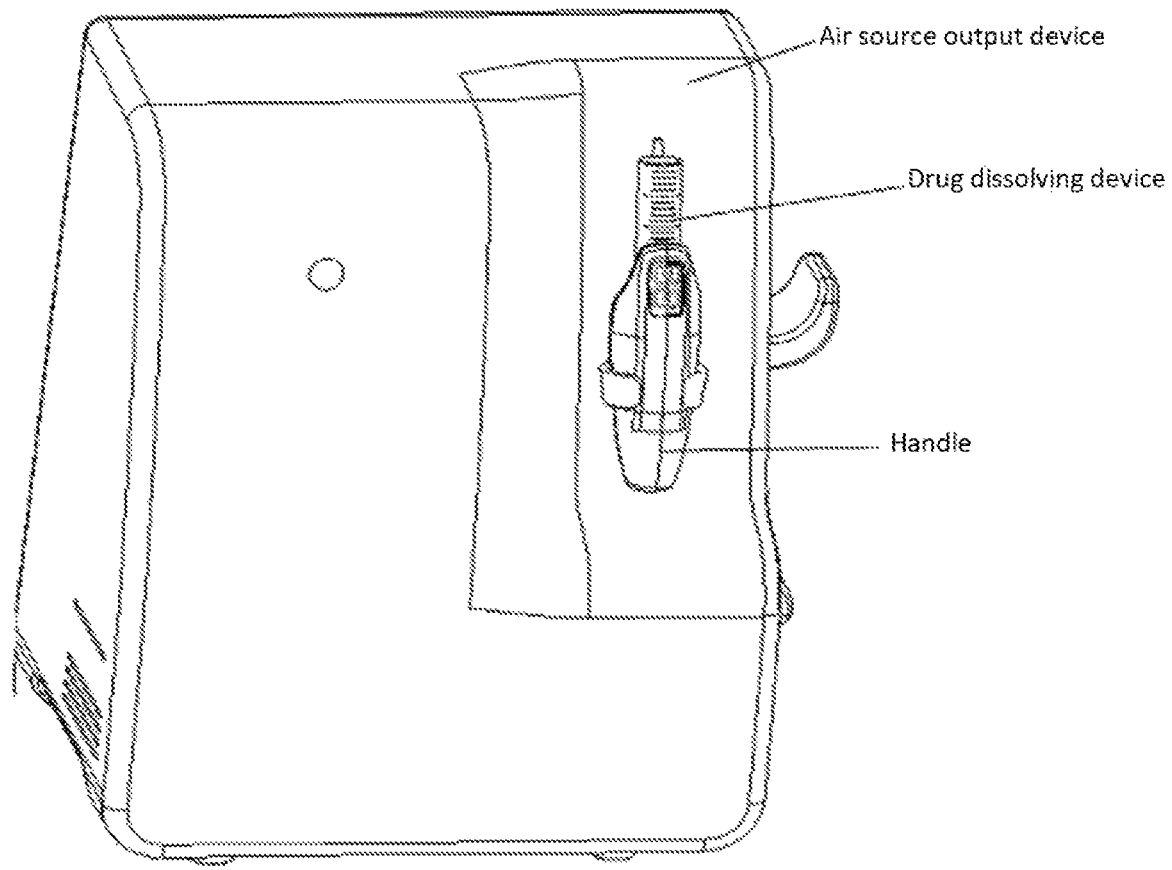
FIG. 6 is a structural view of a sterile drug dispensing system of the present invention.

As shown in FIG. 6, a structural view of a sterile drug dispensing system of the present invention is illustrated. The sterile drug dispensing system of the present invention includes the handle of the above embodiments, and further includes a drug dissolving device and an air source output device. The handle is connected to the air source output device through a power cord and the air pipe, and the drug dissolving device is detachably mounted on the handle. The air source output device delivers clean air to the drug dissolving device through the handle to drive a rubber stopper of the drug dissolving device to move, and the filter in the handle cleans the air from the air source output device once again, so as to ensure that clean and sterile air is injected into the drug dissolving device.

The drug dissolving device has a needle, a barrel and a rubber stopper. The rubber stopper is disposed inside the barrel. The drug dissolving device is provided with a strip for use with the detection unit in the handle to detect whether the drug dissolving device has been mounted on the handle, wherein the strip is designed into a semicircular shape on the drug dissolving device, and may also be a circular ring around drug dissolving device, or a semicircular strip, a corrugated strip or the like. When the drug dissolving device is not in use, that is, in an initial position, the end of the drug dissolving device is on the same plane as the rubber stopper without a dead angle to ensure that the small power air source may blow the end of the drug dissolving device and the rubber stopper to become sterilized, thereby further ensuring that the rear cavity of the drug dissolving device is clean and sterile when in use.

Figure 7:
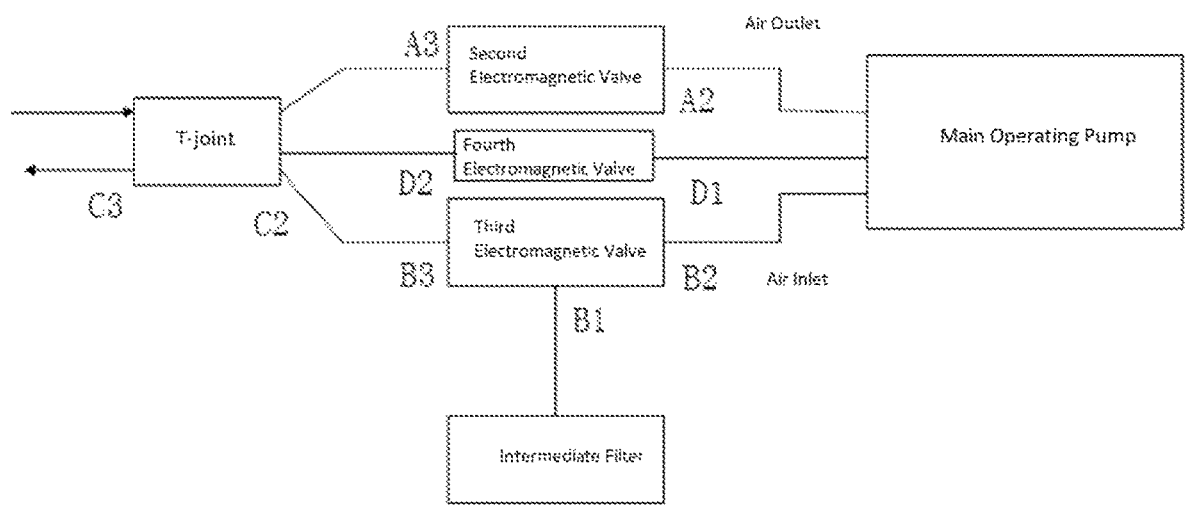
FIG. 7 is a schematic view showing air flow in an air source output device of the sterile drug dispensing system of the present embodiment.

As shown in FIG. 7, a schematic view showing air flow in an air source output device of the sterile drug dispensing system of the present embodiment is illustrated. The main operating pump 21 is always in operation. When a second electromagnetic valve 13 and the third electromagnetic valve 14 are both turned off, the air flows along the intermediate filter, B1, B2, the air inlet, the air outlet, A2, A1, then a purifying pump draws air from the upper tank and the first electromagnetic valve controls the air flow in the pipeline connected to the purifying pump, and then the air is output from the output port 16 through the T-joint to output an air that is smooth, gentle, small-flow clean, which refers to the small power air source; when the second electromagnetic valve is turned on, the air flows along the intermediate filter, B1, B2, the air inlet, the air outlet, A2, A3, C2, C3, and finally outputs from the output port 16 to output an air that is a large flow of clean air, which may be used as a power source, that is, a large power air source; when the third electromagnetic valve 14 is turned on, the air is input from the output port 16, and flows along C3, C2, B3, B2, the air inlet, the air outlet, A2, and A1, and the air is pumped into the air source output device, filtered, delivered to the upper tank, and finally discharged as needed. The main operating pump 21 and the purifying sub-device serve as two different air source outputs, which may provide both a small flow, smooth clean air and a large flow, clean air that may be used as a power source. The user may select above two according to actual needs so that these two have strong practicability. In addition, the above two may be replaced separately when they are renewed, which is convenient and effective to use, and is low in cost.

The dispensing process of the sterile drug dispensing system begins after the drug dissolving device is mounted on the handle, and the air from the main operating pump acts as a power for the movement of the rubber stopper in the drug dissolving device. In actual operation, the operator holds the handle and controls the operation through relevant buttons on the handle. The handle is provided with at least two buttons for controlling the forward and reverse movements of the rubber stopper, which are respectively used for controlling the turning-on and turning-off of the second electromagnetic valve 13 and the third electromagnetic valve 14. When the button for controlling the forward movement of the rubber stopper is pressed, the second electromagnetic valve 13 is turned on, and the air flows along the intermediate-efficient filter, B1, B2, the air inlet, the air outlet, A2, A3, C2, and C3, and after the air is output from the air source output device, the air is injected into the drug dissolving device through the handle and the high-efficient filter in the handle to push the rubber stopper forward for pushing the liquid medicine out from the drug dissolving device. At this time, the front end of the rubber stopper has clean and sterile air, and the rear end has also sterile air. When the button for controlling the reverse movement of the rubber stopper is pressed, the third electromagnetic valve 14 is turned on, and the air is drawn from the outside of the air source output device to enter the air source output device via the handle and the high-efficient filter in the handle and flow along the C3, C2, B3, B2, the air inlet, the air outlet, and A2, A1. At this time, a negative pressure region is formed at the tail of the drug dissolving device to attract the rubber stopper to be withdrawn, so that the liquid medicine in the vial may be drawn into the drug dissolving device. In this way, using the buttons to control the rubber stopper for repeated movement is repeated for several times until the dissolving of the liquid medicine is completed.

The replacement for the air at the front end of the handle by the air source output device and the filter by the sterile drug dispensing system may ensure that the cavity of the drug dissolving device remains in the sterile environment throughout the dispensing process so as to guarantee the safety in drug use for the patients.

Embodiment 9

Figure 8:
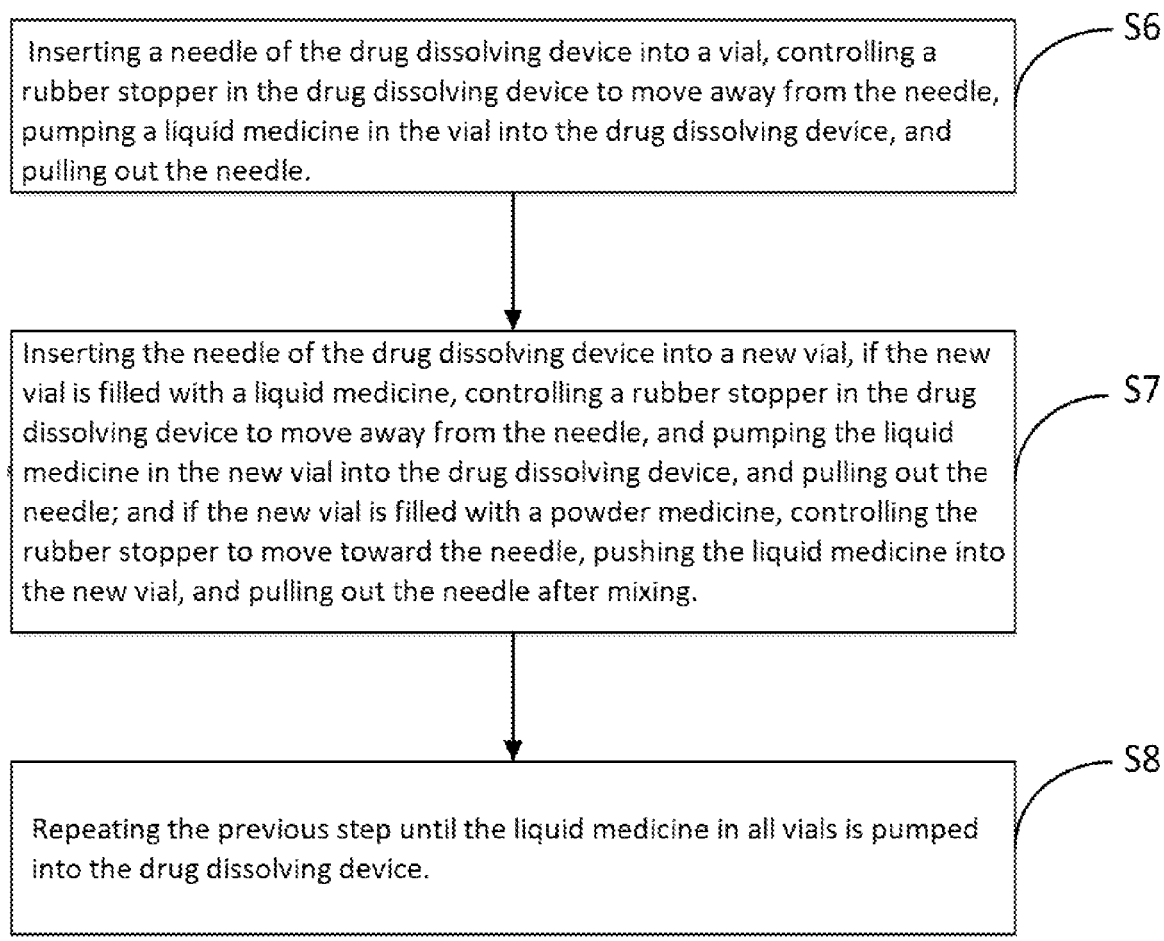
FIG. 8 is a flow chart of a sterile drug dispensing method of the present invention.

As shown in FIG. 8, a flow chart of a sterile drug dispensing method of the present invention is illustrated. The sterile drug dispensing method of the present invention includes the following steps.

Step S6: Inserting a needle of the drug dissolving device into a vial, controlling a rubber stopper in the drug dissolving device to move away from the needle, pumping a liquid medicine in the vial into the drug dissolving device, and pulling out the needle.

Step S7: Inserting the needle of the drug dissolving device into a new vial, if the new vial is filled with a liquid medicine, controlling a rubber stopper in the drug dissolving device to move away from the needle, and pumping the liquid medicine in the new vial into the drug dissolving device, and pulling out the needle; and if the new vial is filled with a powder medicine, controlling the rubber stopper to move toward the needle, pushing the liquid medicine into the new vial, and pulling out the needle after mixing.

Step S8: Repeating the previous step until the liquid medicine in all vials is pumped into the drug dissolving device.

In the sterile drug dispensing method of the present embodiment, a certain distance is reserved between the rubber stopper and the front end of the barrel in the drug dissolving device to counter the negative pressure in the vial. The handle controls the air source output device to extract the air at the rear end of the rubber stopper in the barrel to form a negative pressure environment, so that the rubber stopper moves away from the needle. The handle controls the air source output device to output air to the rear end of the rubber stopper in the barrel to form a positive pressure environment, so that the rubber stopper moves toward the needle. During the operation, it is necessary to ensure that the rubber stopper of the drug dissolving device is controlled to be not moved away from the needle in a polluted environment, that is, the air is not sucked into the front cavity of the drug dissolving device, so as to ensure that the bacteria air may not enter the front cavity of the drug dissolving device, thereby ensuring that the liquid medicine is not contaminated during dispensing.

Embodiment 10

Figure 9:
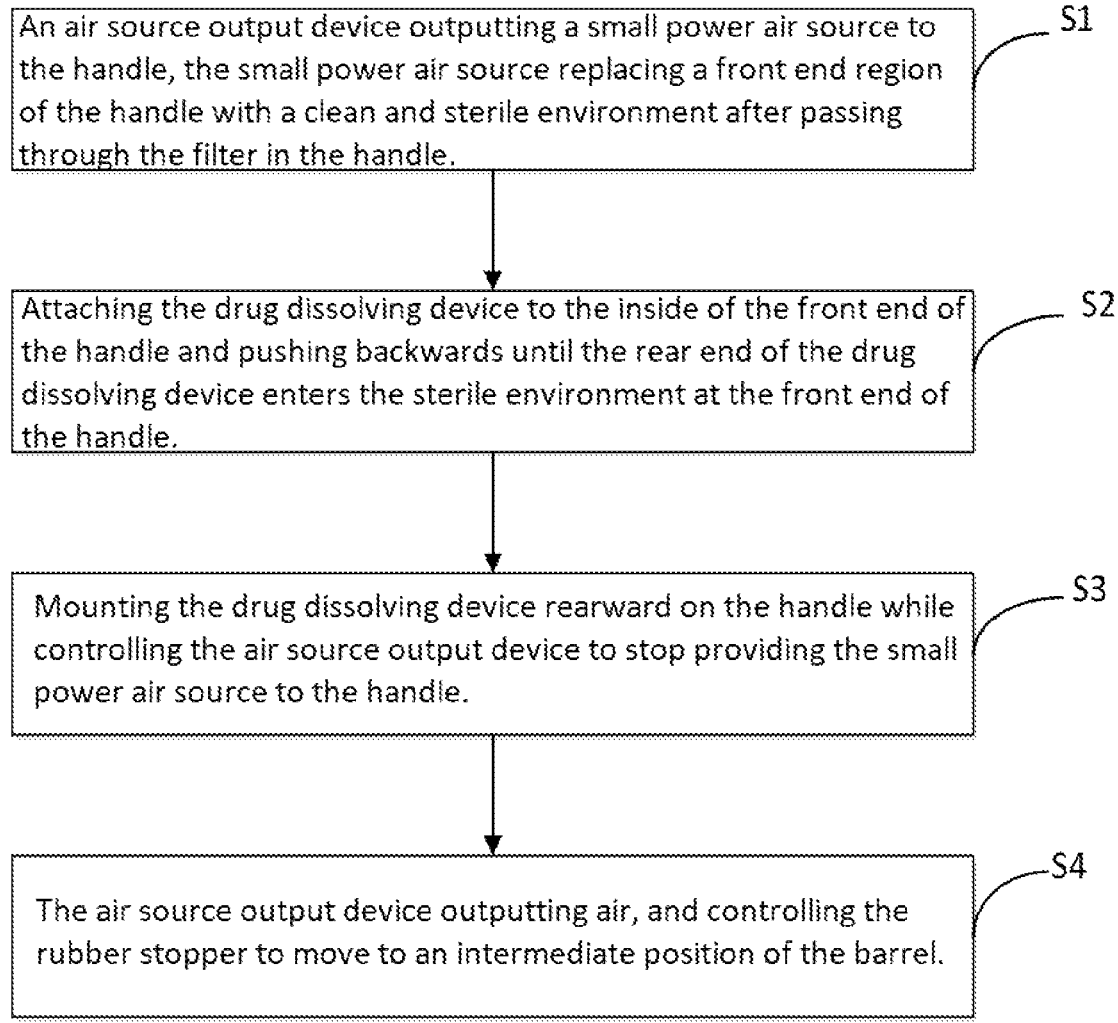
FIG. 9 is a flow chart of a sterile drug dispensing method of the present invention.

As shown in FIG. 9, a flow chart of a sterile drug dispensing method is illustrated. The present embodiment is different from Embodiment 9 in that, before Step S6, the method further includes Step S5: mounting the drug dissolving device on the handle.

Before Step S5, the method further includes the following steps.

Step S1: An air source output device outputting a small power air source to the handle, the small power air source replacing a front end region of the handle with a clean and sterile environment after passing through the filter in the handle.

Step S2: Attaching the drug dissolving device to the inside of the front end of the handle and pushing backwards until the rear end of the drug dissolving device enters the sterile environment at the front end of the handle.

Step S3: Mounting the drug dissolving device rearward on the handle while controlling the air source output device to stop providing the small power air source to the handle.

In Step S1, the rubber stopper of the drug dissolving device is located at the end of the drug dissolving device, and the end of the drug dissolving device is on the same plane as the rubber stopper to ensure that the small power air source may blow the end of the drug dissolving device and the rubber stopper to become sterilized, thereby further ensuring that the rear cavity of the drug dissolving device is clean and sterile when in use.

In Step S2, after the rear end of the drug dissolving device enters the sterile environment at the front end of the handle, it is left for 1-2 seconds to continue mounting, so as to ensure that the small power air source blows the rear end of the drug dissolving device to become sterilized for reaching a clean, sterile environment at the rear end of the drug dissolving device and at the front end of the handle.

In Step S3, when the drug dissolving device is pushed to the groove of the front end of the handle, the drug dissolving device is snapped into the groove of the front end of the handle, and the drug dissolving device is rotated, so as to achieve a snap connection between the drug dissolving device and the handle. The snap mounting is quick and has a good sealing property.

The present invention provides a sterile drug dispensing system, including an air source output device, a handle and a drug dissolving device.

The sterile drug dispensing system of the present invention has the advantages of simple and reasonable structure, good sealing property, easy disassembly and assembly, convenient replacement, safety and reliability, high filtering efficiency, may provide uniform, slow, non-crossing, large-area clean air, and may replace the front end of the handle with a clean and sterile environment for achieving a local level of cleanliness. Through air replacement, the sterile filtering method of the present invention ensures that the drug dissolving device before mounting and during the dispensing, is clean and sterile, safe and reliable, high-efficient in filtration, safe, clean and sterile in filtration, effective in filtration, with reduced labor intensity and wide applicability.

Although the present invention has been described in detail with reference to the foregoing embodiments, those skilled in the art can still modify the technical solutions described in the foregoing embodiments, or replaces some of the technical features equivalently. Any modifications, equivalent substitutions, improvements, etc. made within the spirit and scope of the present invention is intended to be included within the scope of the present invention.

What is claimed is:

1. A sterile drug dispensing method, comprising:
    preparing a sterile drug dispensing system comprising:
        an air source output device;
        a handle;
        a filter is disposed in the handle; and
        a drug dissolving device detachably mountable on the handle; wherein the drug dissolving device comprises
            a needle;
            a barrel; and
            a rubber stopper disposed inside the barrel;
        wherein the handle is connected to the air source output device through a power cord and an air pipe, for filtering air, and controlling the air source output device; wherein the air source output device is used to output and extract air, and
    the method further comprising the following steps:
    Step S6: inserting the needle of the drug dissolving device into a vial, controlling the rubber stopper in the drug dissolving device to move away from the needle, pumping a liquid medicine in the vial into the drug dissolving device, and pulling out the needle;
    Step S7: inserting the needle of the drug dissolving device into a new vial, the new vial being filled with a second liquid medicine or a powder medicine; when the new vial is filled with the second liquid medicine, controlling the rubber stopper in the drug dissolving device to move away from the needle, and pumping the second liquid medicine in the new vial into the drug dissolving device, and pulling out the needle; and when the new vial is filled with the powder medicine, controlling the rubber stopper to move toward the needle, pushing the liquid medicine into the new vial, and pulling out the needle after mixing; and
    Step S8: repeating Step S7 until the second liquid medicine or the powder medicine in the new vial is pumped into the drug dissolving device;
    reserving a certain distance between the rubber stopper and a front end of the barrel in the drug dissolving device to counter a negative pressure in the vial,
    before Step S6, the method further includes Step S5:
    Step S5: mounting the drug dissolving device on the handle;
    before Step S5, the method further includes the following steps:
    Step S1: the air source output device outputting a power air source to the handle, the power air source replacing a front end region of the handle with a clean and sterile environment after passing through the filter in the handle;
    Step S2: attaching the drug dissolving device to an inside of the front end of the handle and pushing backwards until a rear end of the drug dissolving device enters the sterile environment at the front end of the handle; and
    Step S3: mounting the drug dissolving device rearward on the handle while controlling the air source output device to stop providing the power air source to the handle.

2. The sterile drug dispensing method in claim 1, wherein, in Step S6 and Step S7, the handle is configured to control the air source output device to extract the air at a rear end of the rubber stopper in the barrel to form a negative pressure environment, so that the rubber stopper moves away from the needle; and the handle is configured to control the air source output device to output air to the rear end of the rubber stopper in the barrel to form a positive pressure environment, so that the rubber stopper moves toward the needle.

3. The sterile drug dispensing method in claim 2, wherein, in Step S1, the rubber stopper of the drug dissolving device is located at the rear end of the drug dissolving device, and the rear end of the drug dissolving device is on a same plane as the rubber stopper.

4. The sterile drug dispensing method in claim 3, wherein, in Step S2, after the rear end of the drug dissolving device enters the sterile environment at the front end of the handle, it is left for 1-2 seconds to continue mounting.

5. The sterile drug dispensing method in claim 4, wherein, in Step S3, when the drug dissolving device is pushed to a groove of the front end of the handle, the drug dissolving device is snapped into the groove of the front end of the handle, and the drug dissolving device is rotated, so as to achieve a snap connection between the drug dissolving device and the handle.

6. The sterile drug dispensing method in claim 5, wherein, in Step S3, a detection unit is disposed on the handle, for detecting that the drug dissolving device has been mounted on the handle, and controlling the air source output device to stop providing the power air source to the handle.

7. The sterile drug dispensing method in claim 6, wherein, after Step S3, the method further includes Step S4:
    Step S4: the air source output device outputting air, and controlling the rubber stopper to move to an intermediate position of the barrel.

8. The sterile drug dispensing method in claim 7, wherein, the handle is configured to control the air source output device through buttons, and the buttons are disposed on the handle.

* * * * *